United States Patent [19]

Donaghey

[11] Patent Number: 4,631,952
[45] Date of Patent: Dec. 30, 1986

[54] RESISTIVE HYDROCARBON LEAK DETECTOR

[75] Inventor: Lee F. Donaghey, Berkeley, Calif.

[73] Assignee: Chevron Research Company, San Francisco, Calif.

[21] Appl. No.: 770,910

[22] Filed: Aug. 30, 1985

[51] Int. Cl.$^4$ ............................................. G01N 27/12
[52] U.S. Cl. ............................................. 73/23; 338/34
[58] Field of Search ............. 73/23, 27 R, 40, 61.1 R; 338/34, 35; 324/71.5; 340/632, 634; 422/98

[56] References Cited

U.S. PATENT DOCUMENTS

| | | | |
|---|---|---|---|
| 2,826,908 | 3/1958 | Skarstrom | 73/23.1 |
| 3,045,198 | 7/1962 | Dolan et al. | 338/35 |
| 3,427,869 | 7/1965 | Karlbom | 73/73 |
| 3,970,863 | 7/1976 | Kishikawa et al. | 307/116 |
| 4,129,030 | 12/1978 | Dolan | 73/23 |
| 4,224,595 | 9/1980 | Dolan | 338/34 |
| 4,237,721 | 12/1980 | Dolan | 73/23 |
| 4,252,391 | 2/1981 | Sado | 338/13 |
| 4,270,049 | 5/1981 | Tanaka et al. | 250/227 |
| 4,313,338 | 2/1982 | Abe et al. | 338/34 |
| 4,386,269 | 5/1983 | Murphy | 73/40.5 R |

*Primary Examiner*—Stephen A. Kreitman
*Attorney, Agent, or Firm*—S. R. LaPaglia; E. J. Keeling; E. A. Schaal

[57] ABSTRACT

An apparatus and method for sensing organic liquids, vapors and gases which includes a resistivity sensor means comprising an intimate admixture of conductive particles and a material capable of swelling the presence of the liquid, gas or vapor to be detected and an electrical contact thereto.

20 Claims, 12 Drawing Figures

RESISTIVE HYDROCARBON LEAK DETECTOR

BACKGROUND OF THE INVENTION

This invention relates to an apparatus and method of detecting the presence of liquids, vapors and gases. More specifically, this invention relates to an apparatus capable of detecting hydrocarbon liquids and vapors from the change in the resistivity of a detector sensor exposed to those materials.

For widespread commercial use, a particular requirement is a detector's ability to sense hydrocarbons, such as gasoline, leaking from an underground tank into the environment through a change in resistivity of the detector element as it absorbs the hydrocarbons. It is also a requirement to have a detector which operates at ambient temperature, responds quantitatively and reversibly after many exposures, responds over a wide hydrocarbon concentration range, and responds to both liquid and vaporous hydrocarbons. A particular added requirement is a detector sensor with the ability to achieve increased sensitivity by concentrating the hydrocarbons from the environment into the detector, for example, by absorption. Of additional importance is a detector sensor which has the ability to vary its resistance in proportion to the amount of hydrocarbons in its environment.

As contamination of ground water supplies and the detection of noxious vapors in the environment become an increasing concern of the public and subject to greater regulation, it is increasingly important to have a simple straight forward and cost-effective apparatus for detecting these contaminants. The apparatus should be cost-effective, sensitive to low concentrations of the contaminant, and capable of making repeated or continuous monitorings. The device should also have low maintenance and preferably estimate the quantity of hydrocarbons that it is exposed to by the magnitude of change of its response. It would also be desirable if the detector sensor can be retrofitted into existing devices, be immune to false readings and differentiate leaks from naturally occurring background contamination.

Commercial hydrocarbon leak detectors have employed various types of the detection methods and technologies. Thermal conductivity detectors provide continuous monitoring but are high in cost and may require to about ¼ inch of the hydrocarbon on a water surface for detection. Flame combustion detectors are also costly but have the advantage of being contamination proof. However, flame combustion detectors require an energy source such as propane fuel in order to operate and also require frequent maintenance. Catalytic combustion detectors are low in cost and offer high sensitivity. However, they require an energy source to operate at their required elevated temperatures. At these temperatures, the fine wires in the detector are susceptible to corrosion, e.g., from sulfur compounds found in gasoline. The catalyst can be poisoned by additives in gasoline, e.g., lead alkyls. Metal oxide semi-conductor (MOS) detectors are somewhat lower in cost, but they also require an energy source to operate at an elevated temperature. At these elevated temperatures, the fine wires contained in the detector are also susceptible to corrosion. These MOS detectors are undesirably affected by moisture and suffer from drift in base line sensitivity. Carbon detectors are low in cost, but they are undesirably affected by humidity, are mechanically unstable, and are prone to continuous loss of sensitivity. Also, once exposed, they become contaminated and tend not to be reversible. Some carbon detectors require an energy source to operate at an elevated temperature.

The initial detector performs best when detecting liquids while the latter four detectors are primarily useful in detecting vapors. Thus, it would be highly desirable to have a detector sensor and a complete detector which can function adequately in the presence of both contaminant vapors or liquids.

Another approach for a combination gas, vapor, or liquid detector was disclosed by James P. Dolan et al in U.S. Pat. No. 3,045,198. The sensitivity of this apparatus was subsequently improved by operating the device in a non-linear region or in a current saturated mode with an improved detector element as disclosed in U.S. Pat. Nos. 4,237,721; 4,224,595; and 4,129,030. All of these patents are incorporated herein by reference for all purposes.

According to the teachings of the patents, the detector sensor operates by the Van der Waal's absorption forces of the unknown contaminant on a conductive material, such as carbon black graphite or metallic particles, which had been embedded in a resilient base member, such as polyethylene or silicone rubber. The absorption forces of the unknown contaminant on the surface of the conductive particles pulled them apart and caused the resistance of the detector to change. This resistivity change was used to indicate the presence of the unknown and its identity by correlating the resistivity change with the Van der Waal's constant of the unknown gas.

Commercially available devices, embodying the principles of the earliest Dolan et al patent, exhibit a tendency to load up causing the base line reading to shift. In addition, as the particles fall out of the resilient base material, the base line reading also shifts. The more recent Dolan et al patents require the device to be operated in a non-linear voltage range or in a current saturated mode to exhibit enhanced sensitivity. In view of variation between detectors, these ranges or modes must be determined on an individual basis for each detector. This is time-consuming and costly. Furthermore, these ranges or modes will still be subject to base line variations as particles fall out of the detector or they become contaminated.

Thus, it would be desirable to have a detector sensor and detector which can be operated outside a current saturated regime and/or not within the non-linear voltage range. It would also be desirable to have a detector sensor which will not exhibit a base line drift because of the loss of conductive particles during the detector's operation. In addition, it would be desirable to have a detector sensor and detector which does not require a combustible energy source or high temperature to operate around the volatile and hazardous materials to be sensed. Furthermore, it would be desirable to have a detector sensor which would not expose the sensing particles directly to the unknown contaminant which might poison them.

SUMMARY OF THE INVENTION

I have invented a resistive detector sensor, a resistive detector and a process of detecting organic gases, liquids and vapors. My invention possesses the desirable and/or required features recited previously and other advantages readily apparent to the ordinary skilled artisan. The detector sensor can be retro-fitted into commercially available resistive detectors.

The detector, including the detector sensor, detects an exposure to an organic vapor, liquid or gas by measuring a change in resistance across the detector sensor. A change in the measured voltage is caused by a variation in resistance of the detector sensor upon exposure to the organic gases, liquids or vapors.

More particularly, the detector sensor, i.e., resistivity sensor, comprises a swellable matrix which contains an intimate admixture of conductive particles and electrical means for forming an electrical contact thereto. Upon exposure to the vapor, liquid or gas, the matrix swells and thus moves the conductive particles apart relative to each other. This causes an increase in measured resistance by the detector. Intimately admixing the conductive particles within a swellable matrix provides an increased a lifetime and more uniform response for the detector sensor than resistive sensor devices which merely incorporate the conductive particles on the surface of a resilient material where the conductive particles are subject to poisoning by the organic substance, and capable of being knocked off or damaged. Poisoning or loss of conductive particles effects the base line response characteristics of the device. Furthermore, the intimate admixture of the conductive particles within the swellable matrix provides for a more rugged device which can be manufactured in odd sizes and shapes for placement in difficult and/or tight environments such as between the walls in double-wall gasoline storage tanks.

A preferred detector apparatus embodiment also includes the associated electronics necessary to determine the change in resistance of the resistive detector sensor and sound and alarm.

DETAILED DESCRIPTION OF THE INVENTION

Figure 1:
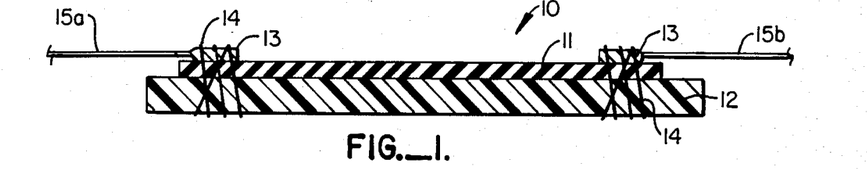
FIG. 1 illustrates a cross-sectional view of an embodiment of a resistive detector of the invention.

The invention will be more clearly illustrated by referring to the FIGS. FIG. 1 is a cross-sectional view of an embodiment of the resistive detector illustrated as 10. The resistive detector 10 includes the resistive-sensing element 11 supported by an insulating substrate 12.

The resistive-sensing element 11 comprises an intimate admixture of a swellable matrix, i.e, material capable of swelling in the presence of the hydrocarbon, gas or vapor to be detected, and conductive particles. For convenience, this mixture is referred to as a swellable conductive matrix or resistive sensor material.

The swellable conductive matrix is preferably selected to exhibit a measurable change in resistivity over the desired concentration range of the organic gas, liquid or vapor to which it is to be exposed and sense. Most preferably, the swellable matrix and the shape of the conductive particles are selected to provide a change in resistivity over the total range of swelling of the swellable matrix.

The swellable matrix should be less conductive than the conductive particles, preferably an electrical insulator, able to absorb and swell upon exposure to the organic substance to be detected without degrading or substantially dissolving, insensitive to water or water vapor, and reversible, i.e., capable of recovering to its original length and conductivity. Preferably the swellable matrix is low cost, has a non-crystalline structure to enhance its solubility toward the organics of interest, and is processable to a substantially uniform compositional mixture with the conductive particles. Examples of suitable materials are synthetic rubber, polyvinyl chloride, polymethyl methacrylate, Tygon ®, silicone and the like. Silicone is preferred.

The conductive particles should be more electrically conductive than the swellable matrix. Preferably, the particles are inert to the organics to be sensed and to water or water vapor, and sufficiently smooth surfaced so as not to tear the swellable matrix. Suitable sizes are less than 100 microns. Preferred sizes range from about 0.001 to about 10 microns and most preferably, from about 0.01 to 1 micron. Long fibrous shapes which can be mixed within the swellable matrix to overlap are preferred for a swellable matrix that swells more than 25% upon exposure to organics. Examples of conductive particles are gold, platinum, silver, copper, nickel, stainless steel, ferrite, electrically conductive carbon, and the like. Conductive carbon blacks are preferred because of their low cost and general inertness to organics.

When forming the detector sensor 11, the intimate admixture of the processable and/or uncured swellable material should include sufficient conductive particles to form a conductive path through the swellable conductive matrix. The ratio of swellable matrix and conductive particles can range from about 1 part swellable matrix to from about 0.25 to about 4 parts conductive particles. An optimum volume ratio of swellable matrix to conductive particles is about 1:1.

An example of a suitable material is taught in U.S. Pat. No. 4,252,391 incorporated herein by reference. Another example of a suitable material is sold under the trade name of SC-CONSIL by the Tecknit Company.

The thickness of the swellable conductive matrix 11 is a function of the expected concentration of gas, liquid or vapor to be encountered and the desired response time. The thinner the material, the faster the response. A suitable thickness is from about 0.001 to about 1 centimeters and preferably about 0.01 to about 0.1 centimeters.

A preferred swellable conductive matrix, when the detector is designed to sense hydrocarbon gases, is a silicone rubber and sufficient conductive particles to form a conductive path through the swellable matrix. Suitable silicone rubbers are marketed by manufacturers such as General Electric Inc. or Dow Chemical Inc. Preferably, the particles are about 0.1–0.3 microns in diameter and without sharp edges which might tear the silicone. Preferably, the conductive particles are conductive carbon black. A preferred detector material is an intimate blend of from about 1 to about 2 parts of Raven carbon black, a product of the W. R. Grace Company, and about 1 part of RTV silicone polymer, a product of the General Electric Inc. These carbon particles have a mean diameter of about 0.3 microns. A particularly preferred composition is a 1:2 mixture of RTV silicone rubber to conductive carbon black.

Optionally, to extend the life of the resistive detector 10, the swellable conductive matrix 11 includes an additional further thin coating of pure swellable matrix, not illustrated, surrounding the swellable conductive matrix, i.e., the intimate admixture of the swellable material and conductive particles.

A conductive tab 13 of any suitable conductive material such as gold, copper, aluminum, and the like is placed in electrical contact with swellable conductive matrix material 11. The conductive tab 13 intimately contacts the swellable conductive matrix sensor material 11 through suitable pressure-binding wirings 14. Suitable wire binders can be any material capable of firmly pressing and pressuring tab contact 13 into swellable conductive matrix 11 to form an electrical contact thereto. Finally, wire leads 15a and 15b electrically contact conductive tab 13.

Figure 2:
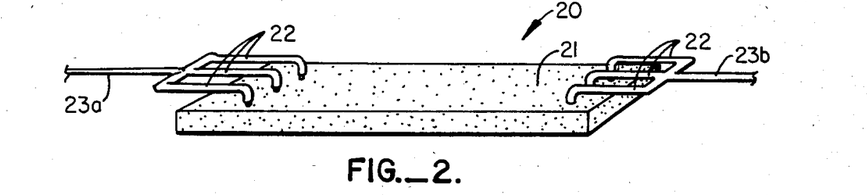
FIG. 2 illustrates an alternative embodiment of the resistive detector.

FIG. 2 illustrates an alternative embodiment resistive detector 20. The detector 20 comprises the resistive sensor material 21, i.e., swellable conductive matrix. Sensor material 21 corresponds to material 11 described in FIG. 1. However, the resistive detector material 21 is contacted by a wire pin insert 22 passing therethrough to form an electrical contact thereto. Suitable wire pin contacts are available from Vector Co. through Newark Electronics, Hayward, Calif. This type of device is completed again with wire leads 23. This embodiment is suitable for use in areas where the device must take advantage of the flexibility of the sensor material 21 without the requirements of a rigid support 12, illustrated in FIG. 1.

Figure 3:
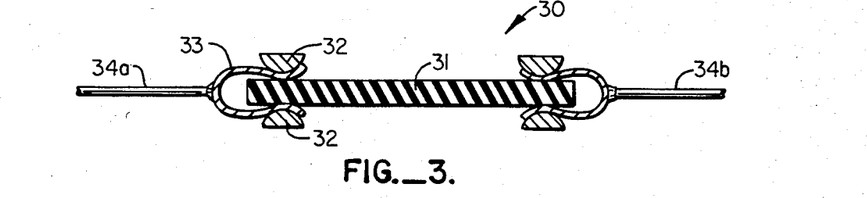
FIG. 3 illustrates a cross-sectional view of another alternative embodiment of the resistive detector.

FIG. 3 illustrates a further alternative sensor 30 containing resistive sensor material 31 corresponding to sensor material 21 in FIG. 2, and sensor material 11 in FIG. 1. In this embodiment, a U-shaped metal or conductive contact 33 is intimately pressed into contact with resistive sensor material 31 through compression elements 32. Suitable pressure elements are available from Vector Co. through Newark Electronics Co., Hayward, Calif. The sensor is completed with wire leads 34a and 34b. The detector 30 is also suitable for environments which can advantageously use the flexibility of the sensor material, but where puncturing the sensor material is undesirable.

Figure 4:
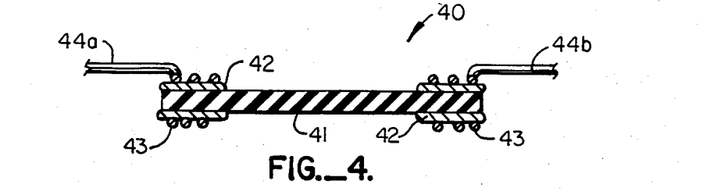
FIG. 4 illustrates a cross-sectional view of a further alternative embodiment of the resistive detector.

A further detector sensor is illustrated in FIG. 4 as resistive sensor 40. Sensor 40 utilizes sensor material 41 corresponding to the previously mentioned materials 11, 21 and 31. The sensor material 41 is contacted with a conductive paste 42 such as a gold or silver paste and thereafter contacted by suitable conductive metal wirings 43 with wire leads 44a and 44b extending from wire windings 43.

Figure 5:
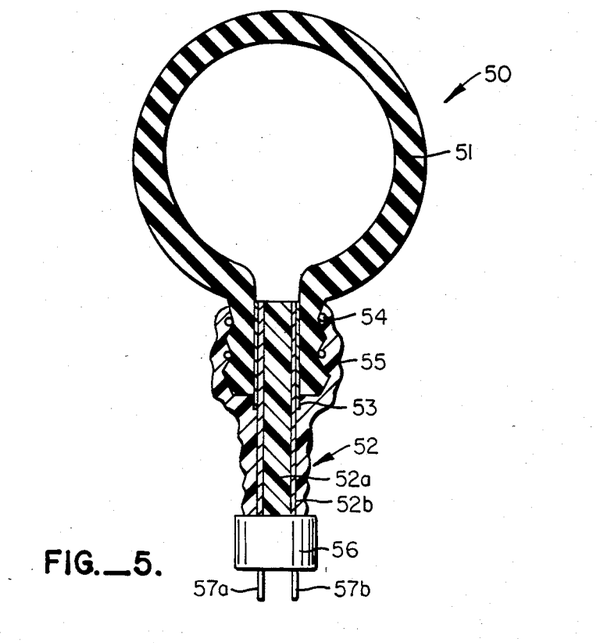
FIG. 5 illustrates a cross-sectional view of an additional alternative embodiment of the resistive detector.

A still further resistive sensor detector is illustrated in FIG. 5 as resistivity sensor 50. The resistive sensor includes the swellable conductive matrix material 51 fabricated in the form of a tube shape. The tube shape is prepared by curing silicone containing fine carbon particles in an appropriate form or mold. A rectangular section of tube is cut through on one side so as to produce the horseshoe-shaped unit of a resistive sensor material illustrated as 51. A conductive support such as a printed circuit board 52 is inserted between the separated portion of the tube. The printed circuit board 52 has an insulating region 52a of a material, such as glass, plastic, epoxy, and the like. An outer coating of a conductive material 52b such as electrolysis nickel, solder, copper or combinations thereof and the like, contacts 52a. The sensor material 51 electrically connects the metalized portion 52b of the board 52 through a highly conductive metal portion 53 by suitable means 54 such as cotton threads or metal threads and the like. The unit is finished with a coating of epoxy material 55 or other suitable sealing means surrounds the contacting portion of sensor material 51 to the circuit board 52 of the sensor 50 as illustrated. The sensor material 51 and circuit board 52 is in electrical contact with any suitable connector 56 having suitable wire leads or other connections illustrated as 57a and 57b.

Figure 6:
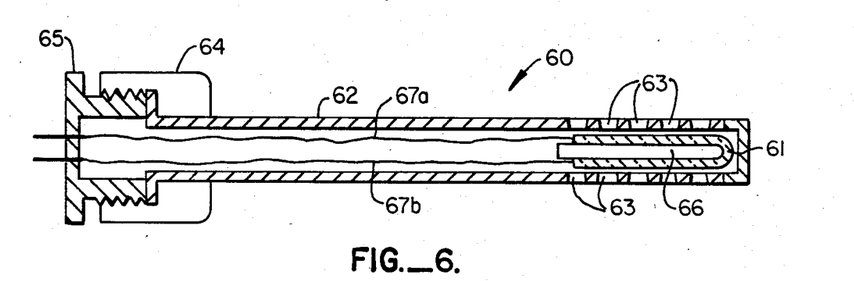
FIG. 6 illustrates a cross-sectional view of the detector portion of the device.

FIG. 6 illustrates a cross-sectional view of a further embodiment of detector sensor portion 60 of a hydrocarbon leak detector. The detector portion 60 includes a resistive sensor material 61 surrounded by a casing of a suitable material which can protect the sensor 61. The casing 62 is configured to avoid interfering with any of the measurements or having an adverse reaction with the material to be detected. An example of a suitable material for the casing 62 is teflon or polyethylene and the like. The casing 62 includes perforations or holes 63 which permit the entrance of the hydrocarbon vapor, liquid or gas to be detected by the detector resistor sensor element 61. The casing 62 further includes a connector 64 for connecting the detector 60 to the body 65 of an apparatus containing the resistance measuring circuitry. Wires 67a and 67b within the casing 62 connect the detector resistivity sensor 61 to the body 65 of the apparatus. To shorten the length of the detector 60 while providing a maximum detector area, the sensor 61 can be folded around an insulating material 66, such as glass, plastic and the like.

It should be clear from the previous embodiments that the resistive sensor can take on any shape or form so long as an electrical contact is made thereto. This permits the detector to be configured into any shape desired for a particular application or job.

The resistivity sensors 10, 20, 30, 40, 50, and 60 are electrically connected to any suitable resistance measuring circuit such as a wheat stone bridge, illustrated in U.S. Pat. No. 4,129,030, incorporated herein by reference. An alternative suitable circuit diagram is illustrated by referring to FIG. 7.

Figure 7:
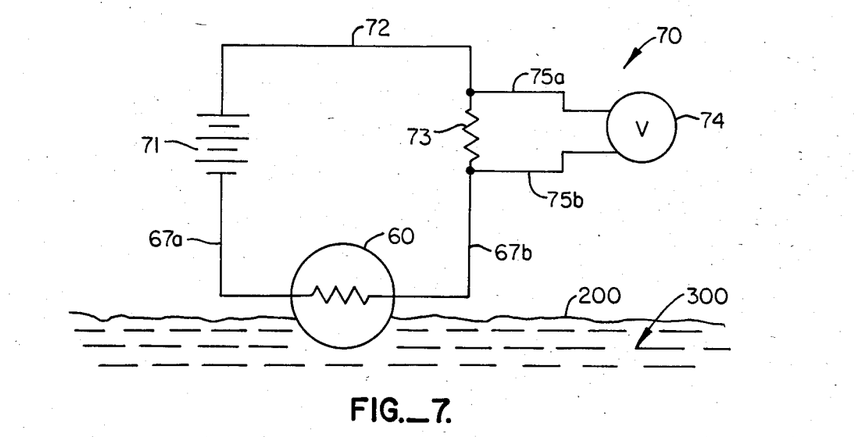
FIG. 7 is a schematic illustration of a circuit diagram used in conjunction with the detector.

In FIG. 7 the schematic of the wiring diagram, includes the detector 60, is illustrated as 70. Although any of the resistivity sensors 10, 20, 30, 40, or 50 could be utilized. The wire 67a is connected to one side of a means for supplying a current and voltage load 71, such as the battery, across the device. The load will vary depending upon the size of the detector area, its resistance and a second known resistor 73 connected in series by wires 67b and 72. A suitable voltage for a detector element having dimensions of about 3 cm×2 cm×0.5 cm is a standard 9-volt battery. The known resistor should have a resistance capable of maximizing the sensitivity of the device. If the resistance is too high, then the sensitivity is too low. A suitable known resistor for the above detector resistor is a 100K ohm resistor. A voltage measuring means 74, such as a volt meter, is connected into the circuit and across the known resistor 73 through wires 75a and 75b.

The apparatus operates by exposing the detector 60 to an organic liquid, vapor or gas to be detected and measuring the change in resistance in the volt meter across the known resistor 73. In FIG. 7, a hydrocarbon liquid 200 is illustrated floating on a liquid such as water 300. The resistivity sensor 61 of the detector sensor 60 absorbs the hydrocarbon 200 and changes its resistance. The change in resistance is measured by the volt meter 74. A detector having a detection element of the dimensions recited above when exposed to unleaded gasoline vapor or unleaded liquid gasoline floating on water is capable of detecting concentrations as low as 0.2 part per million of the hydrocarbon. The response time, of course, is a function of the concentration, but for a detection of about 5 ppm, a normal response time is about 1 minute on water and 10 minutes for vapor exposure. Upon removal of the device from exposure to the hydrocarbon, the base line response of the device returns to 0 after the hydrocarbon liquid or vapor has evaporated.

Figure 8:
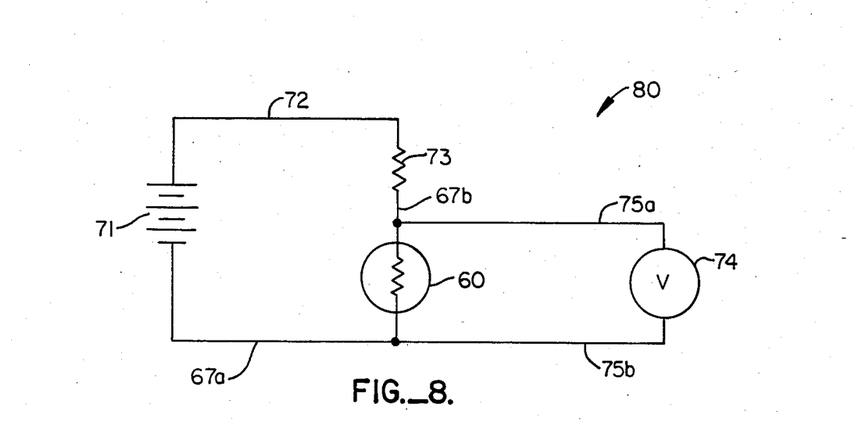
FIG. 8 is an alternative circuit diagram for the detector apparatus.

FIG. 8 illustrates an alternative device schematic illustrated as 80. The schematic of device 80 is identical to device 70 with the exception that the change in voltage of the device 80 is made across the detector 60 as opposed to the known resistor 73.

The resistivity sensor material in a resistivity sensor of the present invention can detect organics dissolved in water, such as gasoline. A silicone type swellable matrix with carbon particles of the type illustrates as sensor 30 in FIG. 3 connected to the circuit shown in FIG. 8, was immersed in laboratory tap water. It was oriented horizontally and held 0.2 cm below the water surface. The volt meter 74 was connected to a recorder. Gasoline was added to the surface of the water. The sensor resistance began to increase slowly with time. After 15 minutes the sensor resistance had increased by 0.41% from its initial value. The time constant for the response was about 15 minutes. Upon removal of the sensor 30 from the water and the evaporation of the gasoline, the volt meter returned to 0 and the response of the recorder returned to the baseline.

Figure 9:
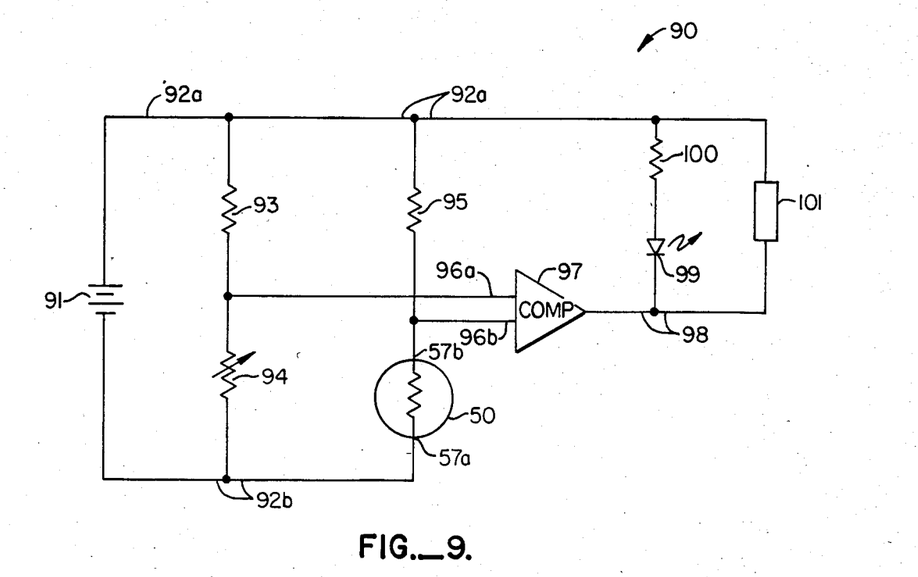
FIG. 9 is a further alternative circuit diagram including the resistive detector and containing an alarm and light signal.

A still further alternative circuit diagram is illustrated in FIG. 9 as 90. This arrangement was specifically designed utilizing a resistive sensor 50 illustrated in FIG. 5. The resistive sensor 50 is connected to one side of a battery 91 through wires 57a and 92b. The opposite side of the sensor is connected to the comparator 97 through wires 57b and 96b and in series with resistor 95. The other input of the comparator is connected from resistor 93 and variable resistor 94 by wire 96a. Resistors 93 and 95 are connected to the opposite pole of the voltage source 91 by wires 92a. The output of the comparator 97 is connected in parallel to an LED 99, a sonic alarm 101, and a fourth resistor 100 through wires 98. A suitable value for the voltage source 91 is a 5-volt battery. Resistors 93, 94, 95 and 100 are 50K ohms, variable between 0 and 50K ohms, 100 ohms, and 500 ohms, respectively. Of course, the resistances could be varied to vary the speed of the detector 90 and/or based upon the selection of the requirements of the comparator 97.

The comparator puts out an output of either 0 or 1 depending upon the input. When detector 50 is exposed to organic vapors such as hydrocarbon vapors and its resistance drops, the input voltage to comparator 97 rises to 5 volts which causes an output to light the LED 99 and/or sound of the sonic alarm 101. The detector circuit is, in essence, a bridge detection system to determine the resistance of an unknown resistor 50 and powered alarm circuit based upon values of the sensor 50. The detector scheme as described for 90 is ideally suitable for placement between the walls of the double-wall tank or below an in-ground gasoline tank to detect any escaping hydrocarbons. The device can remain dormant for months or years and is activated only upon the leaking of the hydrocarbon fuel.

A resistivity sensor 10, 20, 30, 40, 50 or 60 (10–60) including a sensor material 11, 21, 31, 41, 51, or 61 (11–61) comprising two parts of Raven 410 carbon black and one part RTV silicone polymer is capable of detecting many organics. For example, it can detect hydrocarbons or chlorohydrocarbons, such as unleaded regular gasoline, leaded gasoline, diesel fuel, jet A fuel, toluene, n-xylene, methyl alcohol, n-hexane, cyclohexane, methylpentane, trichloroethylene, chloroform, dichloromethane, dichloroethylene, benzene, 2-methylpentane, methylcyclopentane, isooctane, n-heptane, ethylbenzene, butylbenzene, hexyl alcohol, isopropyl alcohol, and octane.

Table I, below, summarizes the resistivity sensor response to over 30 hydrocarbons. The response factors shown are based on the following fact deduced from experiments: the logarithm of the sensor resistance varies nearly linearly with hydrocarbon concentration. The response factor is defined as $$k = \frac{\log(R/R_i)}{P}$$

where $R_i$ and $R$ are the initial and final sensor resistances before and after exposure, and $P$ is the hydrocarbon concentration in volume per volume. Liquid response coefficients are defined with $P$ set arbitrarily equal to unity.

TABLE I

| | Resistance Sensor Response to Hydrocarbon Vapor | | |
|---|---|---|---|
| | Vapor | | |
| | Vapor | Relative | Liquid |
| Hydrocarbon | Response Coeff. (ppm −1) (1) | Resistive Response to 1000 ppm (2) | Liquid Response Coeff (3) |
| butyl benzene | 196.6 | 1.573 | >3.5 |
| octane | 165.8 | 1.465 | >3.5 |
| hexyl alcohol | 165.4 | 1.464 | 1.46 |
| ethyl benzene | 139.9 | 1.380 | >3.5 |
| leaded regular gasoline | 134.2 | 1.362 | >3.5 |
| unleaded premium gasoline | 133.5 | ·1.360 | >3.5 |
| unleaded regular gasoline | 110.0 | 1.288 | >3.5 |
| m-xylene | 86.74 | 1.221 | >3.5 |
| Jet-A | 80.91 | 1.205 | >3.5 |
| toluene | 40.82 | 1.098 | >3.5 |
| isooctane | 39.67 | 1.096 | >3.5 |
| n-heptane | 36.90 | 1.089 | >3.5 |
| diesel | 26.04 | 1.062 | >3.5 |
| trichloroethane | 18.99 | 1.045 | >3.5 |
| cyclohexane | 16.49 | 1.039 | >3.5 |
| benzene | 12.42 | 1.029 | >3.5 |
| methyl cyclopentane | 11.03 | 1.026 | >3.5 |
| dichloroethane | 10.70 | 1.025 | 2.23 |
| n-hexane | 9.81 | 1.023 | >3.5 |
| methyl ethyl ketone | 8.45 | 1.020 | >3.5 |

TABLE I-continued
Resistance Sensor Response to Hydrocarbon Vapor

| Hydrocarbon | Vapor Response Coeff. (ppm −1) (1) | Vapor Relative Resistive Response to 1000 ppm (2) | Liquid Liquid Response Coeff (3) |
|---|---|---|---|
| chloroform | 8.19 | 1.019 | >3.5 |
| 2-methyl pentane | 8.01 | 1.018− | >3.5 |
| methyl tert butyl ether | 7.81 | 1.018 | >3.5 |
| methyl pentane | 7.45 | 1.017 | >3.5 |
| tert butyl alcohol | 7.30 | 1.017 | >3.5 |
| isopropyl alcohol | 4.07 | 1.009 | 2.12 |
| dichloromethane | 1.94 | 1.004− | >3.5 |
| ethanol | 1.29 | 1.003 | >3.5 |
| methanol | 0.648 | 1.002 | >3.5 |
| City Service CitCn 100 n | — | — | 1.56 |
| Chevron bright stock | — | — | 0.420 |
| silicone fluid | — | — | 0.205 |

Notes:
(1) Vapor Response Coeff. $K_v = \log (R/R_{init})/P(ppm)$
(2) Relative Resistive Response = $R - 1000$ ppm/$R_{init}$
(3) Liquid Response Coeff. $k_1 - \log (R/R_{init})$ The actual response time of the device can be altered by varying the size, area, and conductivity of the sensors 11-61. Thus, the detector can be optimized to detect a specific organic compound. When tested against water, salt water, acid, base and chloride in solutions, there was no change. The detectors were left in their exposed state for 3000 hours, but still returned to their original readings after the hydrocarbons or halohydrocarbons were removed.

Figure 10:
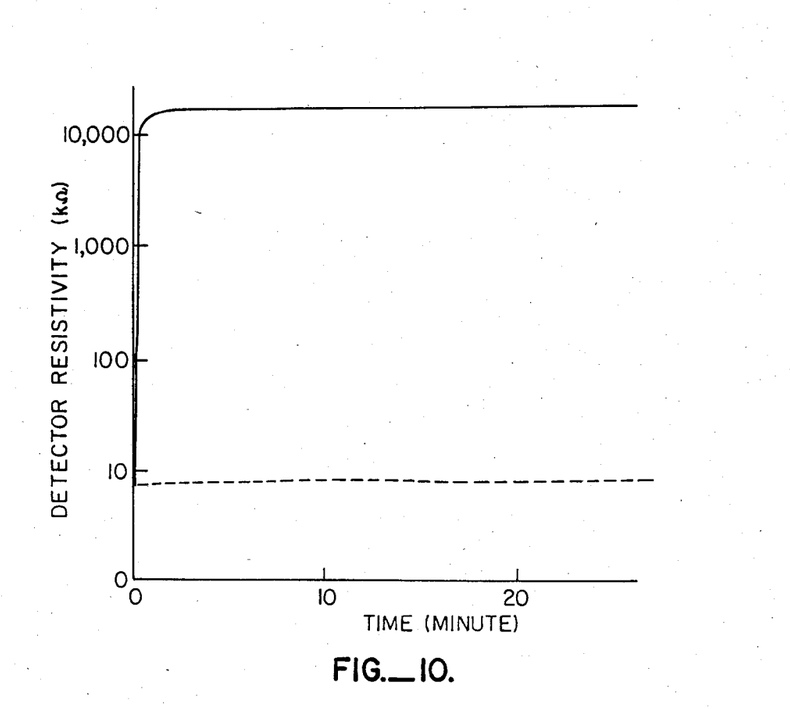
FIG. 10 illustrates the stability of a resistive detector of FIG. 1.

FIG. 10 illustrates a response curve for a resistivity sensor exposed to pure toluene vapor for 26 days. The sensor was fabricated from carbon particles in a silicone matrix in a ratio of 2 parts carbon particles to 1 part silicone rubber. The solid line illustrates the response of the sensor to toluene. As illustrated, the sensor exposed to toluene vapor changed its resistance from 9K ohms to 12000K ohms, then the resistance remained level for 26 days without change. However, upon removal from exposure to toluene, the sensor returned to its original 9K ohm resistivity. The sensor was also exposed to tap water, salt water, 4% to 100% saturation, dilute acid pH 4, dilute base pH 10, and a chlorox solution individually in mixtures to measure its response. The dash line indicates that the sensor is not affected by these materials thus making it an ideal sensor to detect the presence of an organic such as a hydrocarbon or a halohydrocarbon without contamination from ground water, tap water, and the like.

Figure 11:
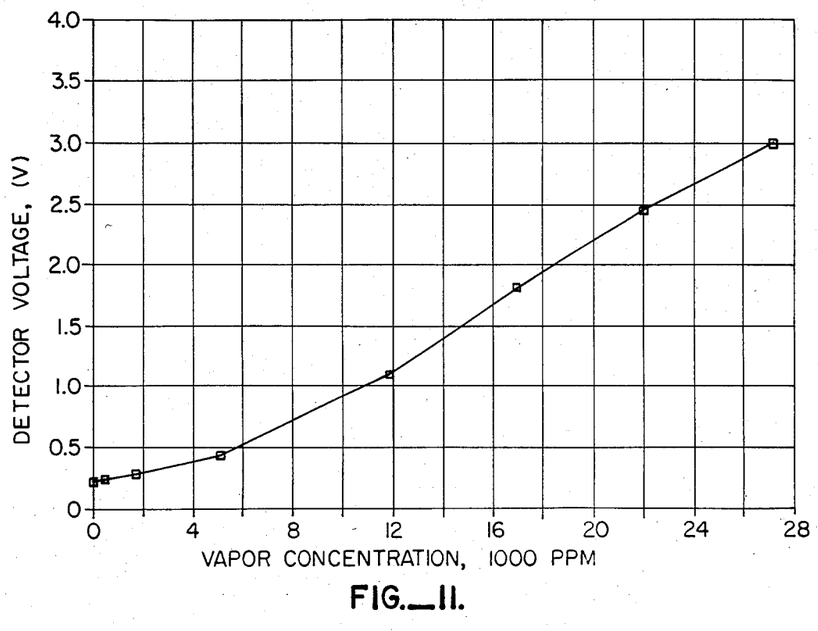
FIG. 11 illustrates the resistive detector response to gasoline vapor.

FIG. 11 illustrates the change in voltage measured across the resistivity sensor due to the change in resistance of a detector of the invention when exposed to increasing concentrations of hydrocarbon vapors such as unleaded gasoline. This response provided an effective way to relate the change in resistance of the sensor to the concentration of the hydrocarbon vapors to which they were exposed. The FIG. 11 shows how the equilibrium voltage across the resistivity sensor varied with the concentration of gasoline vapors that it was exposed to. The experimental evidence shows that when a resistivity sensor is exposed to a hydrocarbon vapor, the resistance changes to a value R from the initial resistance $R_i$ by the relation C is equal to K log $(R/R_i)$ where C is the concentration of the hydrocarbon vapor and K is the constant for the given detector. This predictable range permits each sensor to be base line tested before utilization so that its properties can be adequately known and the circuitry can be optimized for the desired concentration ranges at which the alarm in, for example, FIG. 9 can be configured to sound.

Figure 12:
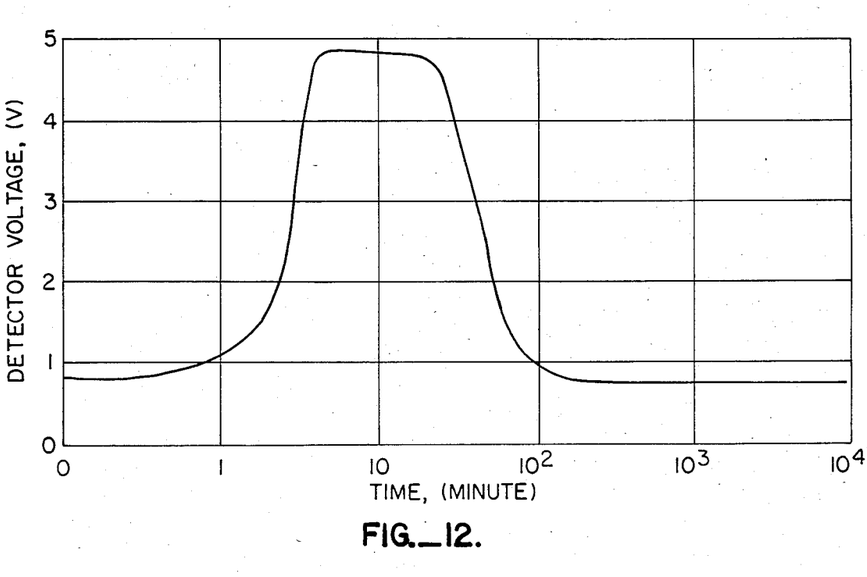
FIG. 12 illustrates the response and recovery of the resistive detector to gasoline on water.

FIG. 12 illustrates how a detector with a sensor having the configuration illustrated in FIG. 3 and connected into the circuitry of FIG. 8 responded to gasoline on water. This response time to peak was several minutes. Upon withdrawal from the gasoline vapors, the detector recovered completely to its initial resistivity as the gasoline evaporated. Thus, unlike certain detectors with sensors which are poisoned upon exposure to the material to be detected, the detector of this invention can be completely reused if it is permitted to recover.

The resistivity sensors can detect hydrocarbon presence in ground water. Groundwater samples were obtained from monitoring wells at gasoline service stations. Samples were removed from wells with a sampling tube and returned to the laboratory in sealed containers.

Silicone/carbon resistivity sensors of the type shown in FIG. 3 were partly immersed in the water samples and connected to the circuit shown in FIG. 7. After 30 minutes the increase in circuit voltage was recorded. then the sensors were removed. The hydrocarbons in the water were extracted with Freon 113 and measured by infrared absorption analysis at 2900 cm$^{-1}$, with gasoline as a standard. The attached table summarizes our results.

TABLE II
Analysis of Groundwater Samples from Service Stations

| Sample | Floating Hydrocarbons | R/Ri (1) Resistivity Sensor | P (ppm) (2) IR Analysis |
|---|---|---|---|
| 1 | No floating oil, bacterial colonies in the water | 1.28 | 98 |
| 2 | No floating oil | 1.85 | 46 |
| 3 | Gasoline sheen from recent spill | 3.23 | 50 |
| 4 | Thin layer of floating oil on water | >1000 | 145 |
| 5 | Thin layer of floating oil on water | >1000 | 165 |

(1) Ratio of resistivity sensor resistance after 30 minutes in contact with water to initial resistance.
(2) IR analysis at 2940 cm$^{-1}$ using Freon 113 extraction of 175 cc water, using gasoline as standard.

The Table II illustrates the ability of the sensor to detect hydrocarbons as illustrated by the increased $R/R_i$ values in the presence of hydrocarbons. Of course, the greater the hydrocarbon concentration as illustrated by Samples 4 and 5, the greater the rise in $R/R_i$. However, even background concentrations of hydrocarbons can be detected or illustrated by the results for Samples 1 and 2.

The invention has been described with reference to particularly preferred embodiments. However, it should be understood that modifications which would be obvious to the ordinary skilled artisan are contemplated to be within the scope of the invention.

What is claimed is:

1. A resistivity sensor comprising:
   sensor means for sensing an organic gas, liquid or vapor, said sensor means comprising an intimate admixture of electrically conductive particles and a material capable of swelling in the presence of said organic liquid, vapor or gas; and
   means for electrically contacting said sensor means.

2. The sensor according to claim 1 wherein the ratio of said swellable material to said conductive particles is in a ratio of from about 1 part swellable material to from about 0.25 to 4 conductive particles.

3. The sensor according to claim 2 wherein said conductive particles have a size of less than about 100 microns.

4. The sensor according to claim 3 further comprising a support means contacting a side of said sensor means, said sensor having opposite ends.

5. The sensor according to claim 3 wherein said means for forming an electrical contact is selected from the group consisting of wire pin contacts, compression contacts, conductive paste and wire binding, metallic tabs and wire bindings, conductive boards carrying insulating means therebetween and insulating filaments providing pressure, and combinations thereof.

6. The sensor according to claim 3 wherein said conductive particles are selected from the group consisting of gold, copper, silver, ferrite, stainless steel, nickel iron, carbon black, conductive carbon, and mixtures thereof.

7. The sensor according to claim 6 wherein said swellable material is selected from the group consisting of synthetic rubber, polyvinyl chloride, polymethyl methcrylate, Tygon ®, silicone, and mixtures thereof.

8. The sensor according to claim 7 wherein said swellable material is silicone.

9. The sensor according to claim 7 wherein said sensor means is an intimate admixture of silicone and conductive carbon particles.

10. The sensor according to claim 9 wherein the ratio of silicone to conductive carbon particles varies from about 1:0.5 to about 1:4 by weight of said silicone rubber and said carbon particles.

11. The sensor according to claim 10 wherein said sensor is a 1:2 mixture of silicone rubber to carbon particles.

12. The sensor according to claim 11 further comprising a layer of substantially pure silicone surrounding said admixture of silicone and carbon particles.

13. An detector apparatus for sensing organic liquids, vapors and gases comprising:
   a resistive detector sensor means comprising an intimate admixture of electrically conductive particles and a material capable of swelling in the presence of the liquid vapor or gas to be sensed, wherein the resistance of said resistive detector sensor means varies according to the concentration of the organic liquid, vapor, or gas to be sensed;
   a voltage supply means electrically connected to opposite sides of said resistive detector sensor means and supplying electrical potential there across;
   a resistive means of known resistance connected in series between said resistive detector sensor means and said voltage supply means; and
   indicating means electrically connected across either said resistive means of resistance or said resistive detector sensor means.

14. The apparatus according to claim 13 wherein said resistive detector sensor means is an intimate admixture of silicone rubber and conductive particles selected from the group consisting of copper, gold, silver, carbon black, conductive carbon, and mixtures thereof.

15. The apparatus according to claim 14 wherein said resistive detector sensor means is an intimate admixture of silicone rubber and conductive carbon particles.

16. The apparatus according to claim 15 wherein said resistive detector sensor means is a 1:2 mixture by volume of said silicone rubber and said carbon particles.

17. The apparatus according to claim 16 wherein said indicating means is electrically connected on opposite sides of said resistive means of known resistance.

18. The apparatus according to claim 17 wherein the indicating means is electrically connected on opposite sides of said resistor detector sensor means.

19. A process for detecting an organic liquid, vapor or gas which comprises:
   applying a current load across a swellable conductive matrix wherein a pole of said current load is connected directly to said swellable conductive matrix and the other pole of said load is connected to said swellable conductive matrix through a resistor of known resistance, said swellable conductive matrix comprising conductive particles and a material capable of swelling in the presence of said liquid, vapor or gas; and
   exposing said swellable conductive matrix to an organic liquid, vapor, or gas.

20. A leak detector kit capable of being assembled to detect organic, gases, liquids or vapors comprising:
   known resistor means; detector means comprising a swellable conductive matrix capable of swelling in response to the organic liquids, vapors and gases to be detected, said detector means including conductive particles within a swellable matrix; power supply means; means for connecting said power supply means, said known resistive means and said detector means in series; and means for connecting said voltage measuring across either said detector means or said known resistor means.

* * * * *